United States Patent [19]

Sulc

[11] 4,362,509

[45] Dec. 7, 1982

[54] DENTAL ATTACHMENT STRUCTURE

[76] Inventor: Josef M. Sulc, 14720 NE. 64th St., Redmond, Wash. 98052

[21] Appl. No.: 208,643

[22] Filed: Nov. 20, 1980

[51] Int. Cl.³ .......................................... A61C 13/22
[52] U.S. Cl. ................................. 433/181; 433/169
[58] Field of Search ............... 433/169, 170, 180, 181, 433/182, 183, 168, 172

[56] References Cited

U.S. PATENT DOCUMENTS

| | | |
|---|---|---|
| 1,324,476 | 12/1919 | Supplee . |
| 1,664,726 | 4/1928 | Adler . |
| 3,171,202 | 3/1965 | Lasky . |
| 3,344,842 | 10/1967 | Cameron . |
| 3,787,975 | 1/1974 | Zuest . |
| 3,868,776 | 3/1975 | Lasky . |
| 3,955,280 | 5/1976 | Sneer .................................. 433/169 |
| 4,193,194 | 3/1980 | Dalise .................................. 433/177 |
| 4,196,516 | 4/1980 | Poveromo ............................ 433/182 |

*Primary Examiner*—Robert Peshock
*Attorney, Agent, or Firm*—Pennie & Edmonds

[57] ABSTRACT

A connector for a dental appliance such as a partial denture, an overdenture or bridge, including a male member, a female member and an element including a body of resilient material mounted by one of the members. The element will be disposed between and in surface-to-surface engagement with the members when they are moved together and engaged telescopically. Mechanical latching structure is provided to latch the element to each member, with the latching structure between the element and the member that supports the dental appliance providing a stronger mechanical latch than that between the element and the member attached to the abutment within the oral cavity.

29 Claims, 9 Drawing Figures

DENTAL ATTACHMENT STRUCTURE

DESCRIPTION

TECHNICAL FIELD

The invention relates to dental attachment structure having applicability in the removable attachment and support for one of a partial denture, an overdenture and bridgework in an oral cavity. The attachment structure includes cooperating attachment members and an element characterized by a sleeve, liner, coating or the like disposed between the cooperating attachment members. One attachment member is permanently located in the oral cavity by a abutment and the other member is mounted on to become a physical part of the removable appliance. The element is formed of plastic, mechanically latched to both attachment members, although more securely to the attachment member mounting the removable appliance, and functions to eliminate wear of the attachment members.

BACKGROUND ART

Dental attachment structure for the removable attachment and support for one of partial denture, an overdenture and bridge in the oral cavity is known to the prior art. Structures as represented generally by Letters U.S. Pat. Nos. 1,324,476 to S. G. Supplee, 1,664,726 to H. A. Adler and 3,787,975 to M. Zuest and others have been used for many years. With regard to the Supplee patent, there is the disclosure of a dental attachment structure including a post member and a sleeve member designed to be telescopically engaged with the post member. Supplee, also, describes a lining, received in position in the sleeve member by a cooperating dent and depression, which functions in the engagement of members in mounting a partial denture in the oral cavity. Engagement is solely through frictional contact between the lining and the post member.

The structure for attachment and support of a partial denture (as disclosed by Adler) essentially duplicates that structure described by Supplee. To this end, the Adler structure includes an independent metal leaf spring providing frictional retention of cooperating members which shall have been telescoped together. As is the case with the Supplee structure, retention of the partial denture described by Adler suffers from the problem of wear of the main components.

The Zuest patent discloses dental attachment structure for removable attachment and support of a partial or full denture in the oral cavity. The attachment structure includes an anchor formed with a socket at the base of a sleeve and a unit for support of the full or partial denture. The anchor is positioned within the root of a tooth which has been endodontically treated. The unit has structure which is attached to the framework of the full or partial denture and a spherically shaped head which is adapted for removable receipt in the socket. The anchor and/or unit are described of being formed of rubber, plastic or metal.

The Supplee, Adler and Zuest dental attachment structures are considered to suffer from various problems and disadvantages, the most important of which may be that of the requirement of repair or replacement of attachment structure in the event that contact surfaces are diagnosed as having become worn. Wear of contact surfaces results from the manner of attachment and support of the appliance within the oral cavity. To this end, the Supplee lining is described as being formed of metal, and most likely a hard metal, to provide the characteristic of elasticity or spring required for retention. Repeated insertion and removal of the appliance results in wear of the post member which ultimately will require repair or reconstruction. The Supplee device is considered to suffer from a further problem, namely a problem that develops from a required shortening of the post member to facilitate mounting to the abutment tooth which may also be short. A shortening of the post member and consequently the sleeve member reduces the area of contact between the lining and the post member, and frictional retention will be limited.

The problem of wear of contact surfaces is considered compounded in the dental attachment structure of Zuest. To this end, Zuest, unlike Supplee and Adler, employs no lining or similar structure so that wear of surface may be diagnosed on either or both of the anchor and unit. Thus, the diagnosis may be such to require replacement of the entire component.

The prior art also includes a form of extracoronal attachment sold by APM-Sterngold of San Mateo, California under the name "Hader Vertical Extension". The Hader extracoronal attachment includes a male member and a female member, and, in use, the male member of a plastic material is cast in metal on the outside of the crown contour of an abutment tooth. The female member is incorporated in an acrylic resin within a hollowed-out plastic tooth of a partial denture. Just as wear of contact surfaces became a problem with the previously referred to prior art dental attachment structures, that problem as well as a problem relating to the strength characteristic of the plastic male member is a problem in Hader structure. A further problem or disadvantage resides in the external placement of the male member of the Hader structure

SUMMARY OF THE INVENTION

The dental structure of this invention may be generally described as including a male member to be permanently mounted on either an abutment within the oral cavity or the removable dental appliance, a female member to be permanently attached to the other of the abutment and removable dental appliance, and an element formed of a resilient material to be received on and mechanically latched to either the male member or female member thereby to reside between and in surface-to-surface contact both with an extension on the male member and the wall of a pocket in the female member when the members are telescopically received by entry of the extension into the pocket. The element is comprised of a replaceable layer of plastic in the form of a sleeve, lining or similar structure. And, the element carries mechanical latching structure to interact with complementary structure both carried by the extension of the male member and the wall of the pocket in the female member. Depending upon the form of the invention, the element will be mechanically latched more securely to the member attached to the removable dental appliance.

In one form of the invention, the male member includes a base and a lug carried on one side of the base for attachment of the male member on the metal framework of the dental appliance. The base may be generally of rectangular outline and the lug, of planar outline, may extend at least along the major length of the base. A plurality of holes are formed along the lug providing an apertured surface for attachment in a casting process or by the agency of a suitable resin. In another form of the invention, the male member includes a base for attachment within a cast coping cemented in a chamfer formed over the root of a tooth. In both forms of the invention, the female member and male member, as heretofore set out, are telescopically received in the mounting of the removable dental appliance in the oral cavity.

The element covers the contact surface(s) of the dental attachment structure in the removable attachment of a dental appliance. The element, thus, serves to obviate problems of wear of components that are difficult or impossible to replace, thereby eliminating difficult repair or an expensive remake of the dental appliance. The element, also, has been found to overcome a common problem of breakage of metal, mechanical latching devices that are constructed as a one-piece unit with an attachment member.

Furthermore, because of the plastic-to-metal contact rather than the seemingly conventional metal-to-metal contact between the male and the female members, the need for precision machining is obviated or reduced substantially and the members may be made by processes of mass production, such as investment casting, while providing a superior fit between members. Other advantages, such as the simple, rapid and inexpensive replacement of a plastic element and the immediate restoration of the original retention and perfect fit of the appliance when required will become clear as the description continues.

BEST MODE FOR CARRYING OUT THE INVENTION

Figure 1:
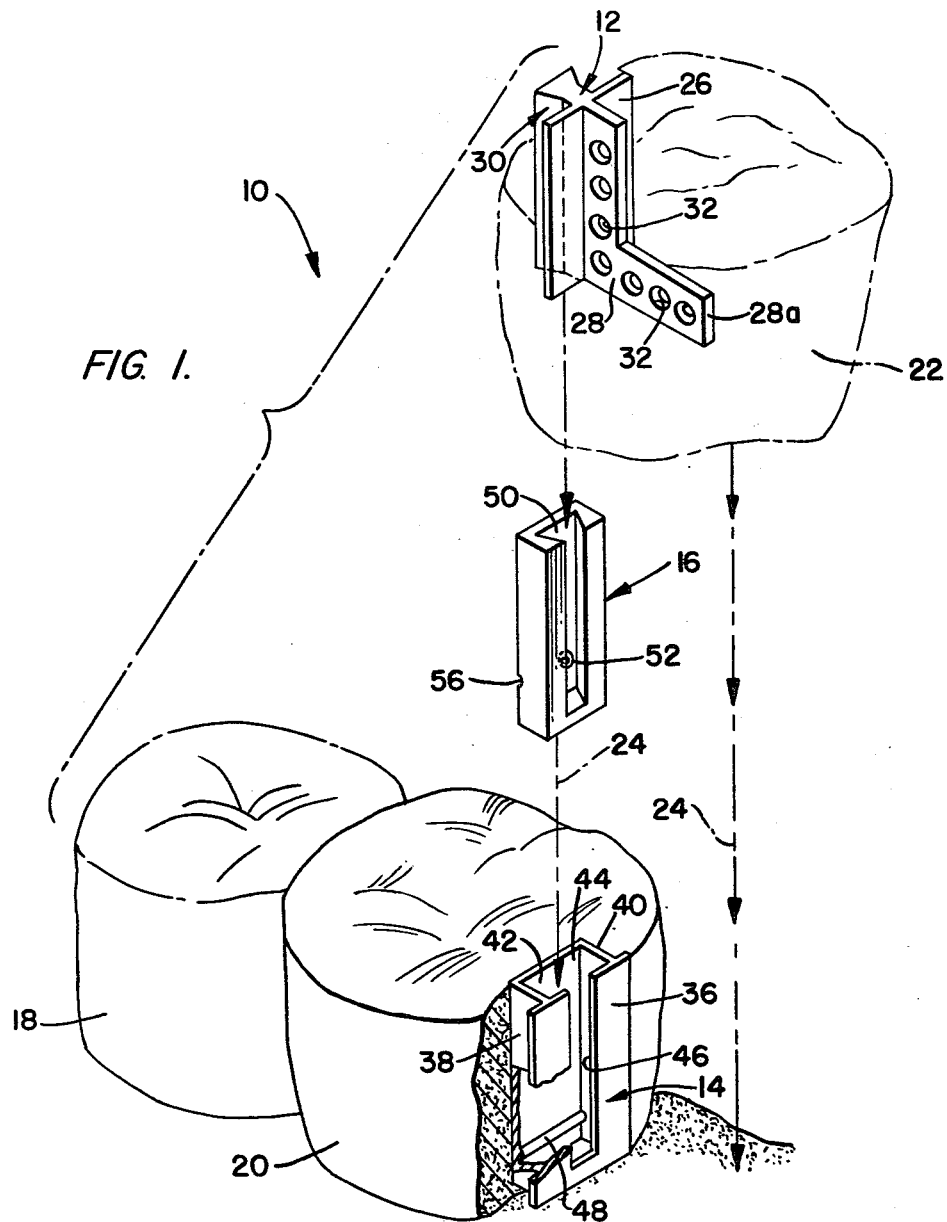
FIG. 1 is an exploded perspective view of an intracoronal connector for use with a partial denture prosthesis.
Figure 2:
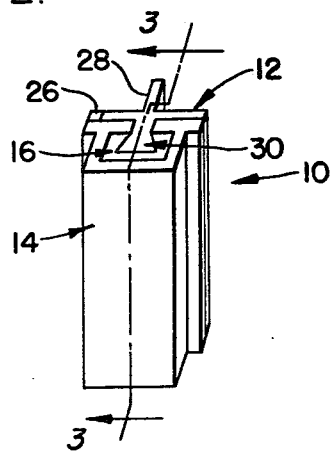
FIG. 2 is a perspective view of the intracoronal connector in assembled form.
Figure 3:
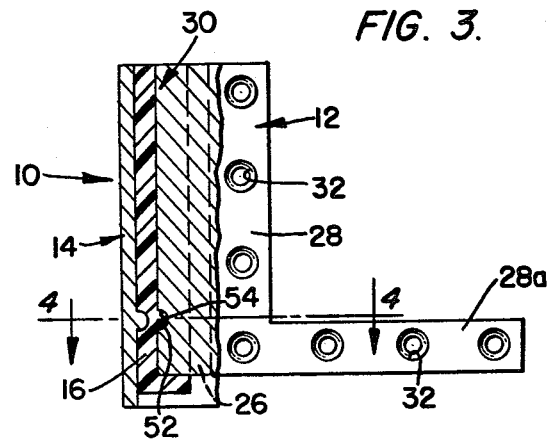
FIG. 3 is a sectional view as seen along the line 3—3 of FIG. 2, illustrating structure for latching components of the connector.
Figure 4:
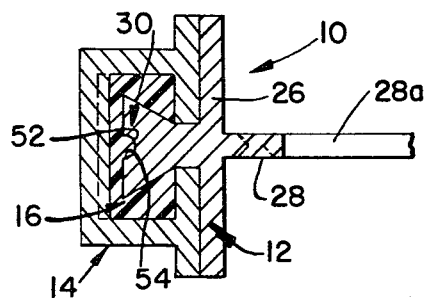
FIG. 4 is a sectional view as seen along the line 4—4 of FIG. 3, illustrating the latching structure in greater detail.

An intracoronal connector 10 for use both with a partial denture prosthesis and bridgework (hereafter "appliance") to permit removable retention of the appliance in the oral cavity may be seen in FIG. 1. The connector includes a male member 12, a female member 14 and an element 16. The element 16 is received on the male member and in the assembled condition, perhaps best seen in FIGS. 2-4, it resides between the male and female members.

FIG. 1 is an environmental view of a portion of the oral cavity illustrating a pair of natural teeth 18, 20 and the appliance 22, comprising one or more teeth, to be removably retained next adjacent to the tooth 20. The teeth 18, 20 and the appliance 22 may be any one of the teeth, such as molars, bicuspids, and so forth.

The male member 12 of the intracoronal connector is attached to the metal framework (not shown) of the appliance 22; while the female member 14 of the intracoronal connector is connected to an abutment tooth 20, as in FIG. 1. The arrows 24 indicate movement telescopically in mounting the element 16 on the male member 12 and the receipt of the male unit (the male member and element) within a pocket of the female member 14 as the appliance 22 is located to a working position in the oral cavity. While not shown, an additional intracoronal connector, such as connector 10, although the structure will be reversed in orientation, may be used to stabilize the appliance to the next adjacent abutment tooth.

The male member 12 includes a base 26, a lug 28 which extends from the base in one direction and an extension 30 which extends from the baase in the opposite direction. The base may be in the form of a flat, rectangular portion. The extension is substantially coextensive with the major dimension of the base and includes an outer end 30a and a web 30b (FIG. 6) which connects the outer end to the base. The outer end is formed to a non-rectangular cross-section, such as that of a trapezoid. The connecting web may be rectangular in cross-section and of a thickness equal to the width of the minor base of the trapezoid from which it extends.

The lug 28, likewise, is substantially coextensive with the major dimension of the base 26 and rectangular in outline. In the form of intracoronal connector illustrated in FIGS. 1-4, the lug includes an extension 28a, also of rectangular outline. The extension is disposed at one end of the lug to provide an overall L-shaped appearance. A plurality of holes 32 are formed along the lug for purposes to be discussed. Preferably, the holes will be located at equidistant spacing along the lug, and its extension.

Figure 6:
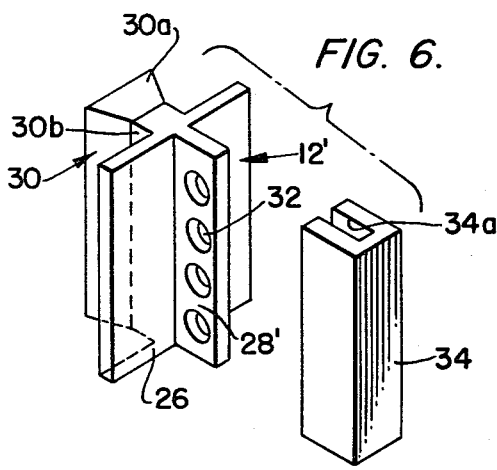
FIG. 6 is a perspective view of a male member of the intracoronal connector, slightly modified from that of FIGS. 1-4 and, also, illustrating a sleeve exploded away from a lug extension.

FIG. 6 illustrates a male member 12' which substantially duplicates the male member 12 described above. This modified form of male member differs from the male member of FIG. 1 with respect to the form of lug 28'. To this end, the lug 28' is complete without extension 28a. A sleeve 34 is associated with male member 12' for purposes as will also be discussed. A channel or pocket 34a permits mounting receipt of the sleeve on the lug 28'.

As previously indicated, the male member 12 (and for that matter male member 12') is attached to the metal framework of the appliance 22. Referring specifically to male member 12', and according to well known techniques, the framework pattern may be waxed directly to sleeve 34 which becomes a part of the wax pattern. In carrying out this technique of attachment of the male member to the metal framework, the sleeve preferably will be formed of plastic or other material which will burn and vaporize with the wax through a sprue in an investment mold. The male member 12', on the other hand, is formed of a metal which is uneffected by the range of temperature of the oven, and will remain in the desired orientation with respect to the investment and the metal framework to be formed. The molten metal to be passed into the sprue will find its way into the investment and to the location of the several holes 32 in the lug 28 of the male member in casting the metal framework directly around the lug.

In a technique that is gaining in favor because of simplicity, and for reasons both of speed of the process and the ability for later adjustment, the male member 12 may be attached to the metal framework by an acrylic resin. In this technique a greater surface area of lug may be required as well as an increased number of holes 32 for stabilization of the male member to the metal framework and the maintenance of the integrity of the connection. Thus, the lug may be L-shape. The acrylic resin which shall have flowed through and set within the holes of the lug provides the attachment. Adjustment is contemplated by an application of heat to soften the resin.

Figure 5:
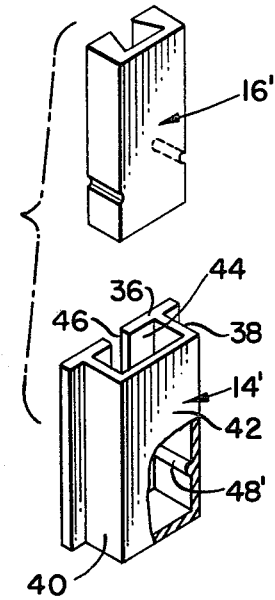
FIG. 5 is an exploded perspective view of certain components of the intracoronal connector, illustrating a slightly modified form of latching structure.

The female member 14 of the intracoronal connector is attached within a full crown or an inlay of abutment tooth 20. The female member includes a base 36 and a pair of walls 38, 40 which extend from the base. The space between the walls is closed by wall 42 thereby to define a pocket 44 along the length of and behind the base. The pocket is closed at the end toward the root (not shown) of the abutment tooth. A slot 46 is formed in the base. The slot extends from the region of the opening into the pocket substantially to the other end and is of a width to accommodate web 30b of the male member. A ridge 48 is formed along the wall 42, within the pocket, as may be seen if FIG. 1. The female member 14' (see FIG. 5), which otherwise duplicates the female member of FIGS. 1-4, provides a pair of ridges 48'. To this end, one ridge 48' is formed along wall 38 and a like ridge (not shown) is formed in a similar location along wall 40. The purpose of the ridge(s) in the female members 14, 14' will be discussed below.

An important aspect of the invention in an intracoronal connector is in the element 16. The element may comprise a layer of plastic, such as Nylon, Teflon or similar material in the form of a sleeve, lining or coating. The element 16 is coextensive in length with extension 30 of male member 12 and of a cross-section to be received snugly in pocket 44 of female member 14, 14'. The element 16, accordingly, may have a rectangular cross-section and includes a cutout 50 of an outline to conform to the shape of the outer end 30a of extension 30. The element, further, includes a projection 52, such as a bulb, within the cutout for mechanically latching in a depression 54 formed on the outer end 30a (see FIGS. 3 and 4) of the extension. The projection is located near the closed end of the cutout.

The element 16 and male member 12 comprising a male unit are mechanically latched to the female member 14. For this purpose, the element includes a groove 56 and mechanical latching is completed by interaction of the groove and the ridge 48 formed within pocket 44.

A similar form of mechanical latching of the male unit comprising the male member 12 (or 12') and element 16' (FIG. 5) with the female member 14' (see also FIG. 5) is contemplated. For this purpose, the element 16' includes a pair of grooves 46' in a position to interact with ridges 48' along the walls 38, 40.

In the positioning of the appliance 22 in the oral cavity, element 16, 16' is received on and latched to extension 30 of male member 12, 12' and then the male unit is telescoped into and latched within the pocket 44 of female member 14, 14'. The assembled position of structure may be seen in FIGS. 2–4 wherein the base 26 of male member 12, 12' is juxtaposed to base 36 of female member 14, 14', the web 30b extends through slot 46 and the male unit is latched within the pocket. The force of mechanical latching of the male unit will exceed that of the assembled unit. Therefore, the male unit will remain intact when the appliance is removed from the oral cavity.

Figure 7:
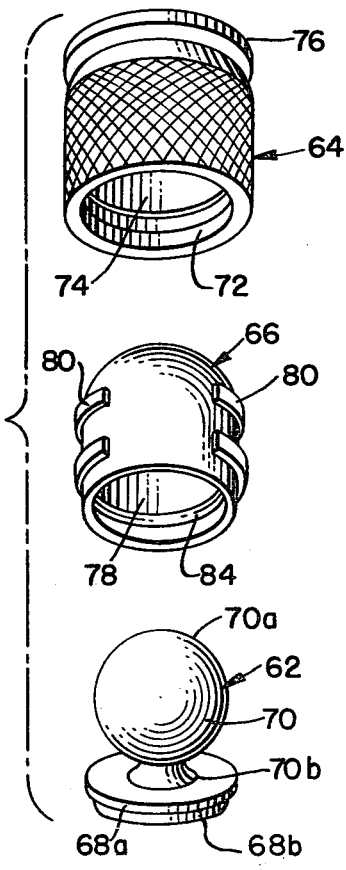
FIG. 7 is an exploded perspective view of a root cap connector for use with an overdenture.
Figure 8:
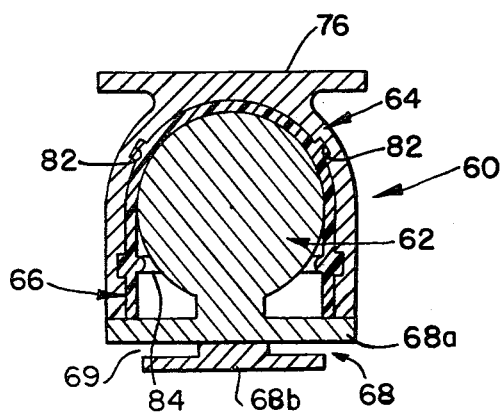
FIG. 8 is a view in elevation of the root cap connector of FIG. 7 in assembled form.

FIGS. 7 and 8 illustrate a root cap connector 60 for use primarily with an overdenture (hereafter "appliance") in the removable retention of the appliance in the oral cavity. The root cap connector 60 includes male member 62, a female member 64 and an element 66 all of which function in a manner similar to the manner of functioning of the component parts of the intracoronal connector 10.

The male member 62 comprises a base 68 and an extension including a spherical end 70a which is supported on the base by a connecting pedestal portion 70b. The base, perhaps best illustrated in FIG. 7, includes at least one and preferably a pair of base members 68a and 68b of a planar, circular shape. The base members are spaced apart by a recess 69 extending toward a neck. Both the neck and the extension are located along the axis of the base.

The female member 64 is in the form of a housing, closed at one end having an opening 72 at the other end which communicates with a substantially cylindrical pocket 74. The pocket is contoured at the closed end to provide a surface complementary to that of the spherical end 70a of extension 70. A flange 76 preferably is located at the closed end of the housing to assist in the creation of a firm connection between the female member and the appliance.

An important aspect of the invention in a root cap connector is in the element 66. Thus, the element is in the form of lining of an outline for receipt within pocket 74 of female member 64 and, in turn, includes a pocket 78 for receipt of the male member 62.

A ridge 80 and preferably a plurality of ridges are formed on the outer surface of the element 66 and a similar number of grooves 82, complementary in outline, are provided in the inner surface of female member 64. The ridges and grooves provide a mechanical latch to maintain the integrity of the female unit when the element is snapped into place. A retention ring 84 is formed within the pocket 78 for purposes as will become clear.

As discussed, the root cap connector 60 has application primarily with overdentures. According to well known endodontic techniques including the surgical removal of the portion of the tooth which extends beyond the gum line, the root of the tooth is prepared for receipt of the male member 62. For example, the root may be chamferred and the male member may be bonded to the top of the root coping. Particularly, the base 68 is bonded to the root coping so that the extension 70 is exposed to receive the female member 64 and the appliance. The coping covering the root surface is made of wax incorporating the male member 62 in it. The recess 69 of the base is imbedded in the wax. Utilizing a casting technique previously described, the coping is cast of an alloy such as gold, mechanically locking the male member made of a higher fusing alloy within it. This unit, then, is cemented over the root in the oral cavity.

The appliance will be removably received by a snap retention as the retention ring first contacts the male height of contour and moves beyond that contour to the location as may be seen in FIG. 8.

During fabrication of the appliance, referring to the overdenture, a spacer (not shown) may be utilized to maintain a space between the end of the female member 64 at the opening 72 and the base 68 of male member 62. A similar space, then, would be located between the spherical end 70a of extension 70 and the inner surface of element 66. Upon delivery of the completed appliance the spacer would be removed. Thus, the appliance may undergo slight vertical movement relative to the root of the tooth. The nature of the construction of the root cap connector, also, permits rotational movement of the appliance relative to the root. As such, the root is protected from excessive forces.

Figure 9:
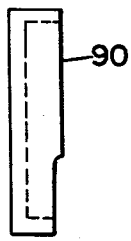
FIG. 9 is a view in elevation of a fabricating element.

The intracoronal connector may be provided with a fabricating element 90 which generally duplicates element 16 (see FIG. 9). The fabricating element may be used on the male member during all stages of partial denture fabrication (impression taking, attachment of the male member to the metal framework of the appliance, and so forth) when mechanical latching of the male unit to the female member is not desired. The fabricating element may also be used to accustom the patient in initial use of the appliance. To this end, the fabricating element is formed with a relievement to the depth of the groove in the region between the groove 56 and the closed end. The fabricating element, similarly, may duplicate element 16'. Thus, the mechanical latching capability of the male unit with the female member is eliminated, and greater ease in manipulating the appliance is achieved.

The element 16 permits the realization of several advantages which are not capable of realization with prior art connectors of the types considered herein. Importantly, and as a main advantage, the element provides unequaled protection of the original male member and/or female member and by the elimination of wear of members the element obviates the heretofore required replacement and consequent repair or reconstruction of the member(s). Members mounted by prior art structures commonly are difficult or impossible to replace, and, accordingly, repair of reconstruction is expensive. According to the invention, only the element, formed of plastic by mass production techniques, such as injection molding or a similar mass production process, is replaced as wear through friction is diagnosed. The element, itself, is relatively inexpensive and by virtue of a degree of resilience it makes unnecessary the need for precision machining of the members heretofore required for metal-to-metal contact support. Actually, it has been found that the element permits a fit superior to the fit of the members which may have been precision machined. Further, still, the element permits the use of dentistry approved alloys, other than alloys of precious metals, which may be of increased hardness, provide higher strength characteristics and be of lower cost. Also, the male and female members may be produced by less expensive techniques, such as investment casting. Finally, the element provides mechanical latching capability. In summary, the element provides unequaled protection of the members, it permits a dramatic reduction both in cost of manufacturing of the appliance and in adapting the appliance to the oral cavity, and it serves in providing overall comfort of wear.

I claim:

1. Dental structure for removable mounting of a dental appliance in the form of a partial denture, overdenture, bridge or similar dental appliance in an oral cavity comprising:

(a) a male member including an extension, means on said member for mounting the same permanently either on an abutment within said oral cavity or said dental appliance to be removably mounted in said oral cavity;

(b) a female member including a housing and a pocket into which said extension is adapted to be telescopically received when said dental structure is mounted in said oral cavity and from which said extension is retracted when said dental structure is removed from said oral cavity, said famale member adapted to be permanently mounted to the other of said abutment and dental appliance; and (c) an element including a body of resilient, non-metallic material, said element adapted to be mounted either by said extension of said male member or in said pocket of said female member whereby when said members are telescopically received said element will be disposed between and in surface-to-surface contact with both said extension and the wall of said pocket both to cushion said member and provide a tight fitting telescopic engagement and prevent any frictional contact of members when received and retracted.

2. The dental structure of claim 1 wherein said mounting means includes a base and a lug, said base being generally of rectangular, planar outline and said lug extending from said base at least along its major dimension on the side opposite to that of said extension.

3. The dental structure of claim 2 wherein said lug is L-shaped in outline.

4. The dental structure of claims 2, or 3 wherein said lug includes a plurality of holes therealong for attachment of said male member to said dental appliance.

5. The dental structure of claim 2 wherein said lug is of rectangular outline and includes a plurality of holes along its length, and said dental structure further includes a sleeve, said sleeve being formed with a slot thereby to be slidably received on and along said lug.

6. The dental structure of claim 2 wherein said extension is formed along the major dimension of said base and includes an outer end of non-rectangular cross-section and a web portion connecting said outer end and said base.

7. The dental structure of claim 6 wherein said outer end is trapezoidal in cross-section and said web is rectangular in cross-section.

8. The dental structure of claim 6 wherein said body is solid, of an outline complementary to the outline of said pocket and includes a cutout having an outline complementary to that of said outer end thereby to achieve said surface-to-surface contact.

9. The dental structure of claim 1 wherein said mounting means includes a base generally of circular, planar outline, and said extension includes an outer end in the form of a spherical ball and a pedestal for supporting said outer end on said base.

10. The dental structure of claim 9 wherein said body is in the form of a lining complementary in outline to said pocket, said lining having an open end, a closed end and a surface therebetween, and said lining residing in said surface-to-surface contact within said pocket.

11. The dental structure of claim 8 or 10 including first attachment means for attaching said body to one of said male and female members, and second attachment means for attaching said body to the other of said male and female members when said members shall have been telescopically received, said first attachment means providing a more secure attachment between structures.

12. The dental structure of claim 11 wherein said first attachment means comprises at least one projection on said body and a cooperating depression for each depression formed on said member.

13. The dental structure of claim 12 wherein said first attachment means includes a single projection in the form of a ball-type protuberance formed in said cutout and a cooperating depression formed on said outer end.

14. The dental structure of claim 12 wherein said first attachment means includes a plurality of projections in the form of a ridge formed on said lining and a cooperating number of depressions formed on said pocket.

15. The dental structure of claim 13 wherein said second attachment means includes at least one ridge within said pocket and a cooperating groove for each ridge formed on said body.

16. The dental structure of claim 15 wherein said female member includes a base and said housing includes a pair of side walls extending from said base and a connecting wall, and said ridge being formed on said connecting wall.

17. The dental structure of claim 12 wherein said second attachment means includes a ridge, said ridge being formed within said lining and around said surface near said open end, said ridge cooperating with a portion of said spherical ball beyond the portion of maximum dimensions when said members are telescopically received.

18. The dental structure of claim 1 wherein said element is formed of a plastic material.

19. The process of mounting an intracoronal dental appliance in the form of a partial denture, overdenture, bridge, or similar dental appliance in an oral cavity comprising:
   (a) mounting one of a male and female member to said dental appliance;
   (b) mounting the other of said male and female members to an abutment in said oral cavity;
   (c) mounting and mechanically latching an element having a body of resilient, non-metallic material to said member mounted to said dental appliance, said element being in surface-to-surface contact therewith;
   (d) receiving said members in telescopic movement to locate said dental attachment in said oral cavity, said element being in surface-to-surface contact with said member mounted to said abutment; and
   (e) mechanically latching said members together, said last-mentioned latching action being less secure so that said element will release with said dental attachment from the latched position when said dental appliance is removed from said oral cavity.

20. Dental structure for removable mounting of a dental appliance in the form of a partial denture, overdenture, bridge or similar dental appliance in an oral cavity comprising:
   (a) a male member including
      (1) a base,
      (2) an extension disposed along a major dimension of said base,
      (3) a web portion connecting said extension to said base, said web portion having a thickness less than the greatest thickness of said extension, and
      (4) a lug extending from said base on the side opposite to that of said extension, at least said lug serving to mount said male member permanently on said dental appliance;
   (b) a female member including a housing providing a pocket into which said extension is adapted to be telescopically received when said dental structure is mounted in said oral cavity and a slot to accommodate movement of said web portion during said telescopic receipt and during retraction of said dental structure from said oral cavity, said female member adapted to be permanently mounted to an abutment in said oral cavity;
   (c) an element including a body of resilient, non-metallic material, said element adapted to be mounted by said extension of said male member whereby when said members are telescopically received said element will be disposed between and in surface-to-surface contact with both said extension and the wall of said pocket both to cushion said member and provide a tight fitting telescopic engagement and prevent any frictional contact of members when received and retracted;
   (d) first mechanical attachment means carried by both said element and extension for mounting said element on said extension; and
   (e) second mechanical attachment means carried by both said element and housing within said pocket for removable securement of said dental appliance within said oral cavity, said first mechanical attachment means providing a mechanical securing capability greater than that provided by said second mechanical attachment means whereby said element when said dental appliance is removed from said oral cavity remains secured to said extension.

21. The dental structure of claim 20 wherein said base is generally of rectangular planar outline and wherein said lug extends along the major dimension of said base throughout a length substantially equal to said major dimension.

22. The dental structure of claim 20 wherein sides of said extension diverge from said web to an outer end of non-rectangular cross section.

23. The dental structure of claim 20 wherein said first attachment means comprises at least one projection on said body and a cooperating depression for each projection formed on said extension.

24. The dental structure of claim 23 wherein said body is solid, of an outline complementary to the outline of said pocket and includes a cutout having an outline complementary to that of said extension, and wherein said first attachment means includes a single projection in the form of a ball-type protuberance formed on said cutout and a cooperating depression formed on said extension.

25. The dental structure of claim 20 wherein said second attachment means includes at least one ridge within said pocket and a cooperating groove for each ridge formed on said body.

26. The dental structure of claim 25 wherein said female member includes a base, said slot located in said base, and said housing including a pair of side walls extending from said base connected by a connecting wall, and said ridge being formed on said connecting wall.

27. Dental structure for removable mounting of a dental appliance in the form of a partial denture, overdenture, bridge or similar dental appliance in an oral cavity comprising:
   (a) a male member including (1) a base generally of circular, planar outline serving to mount said male member permanently on an abutment within said oral cavity, (2) an extension including an outer end in the form of a spherical ball, and (3) a pedestal for supporting said extension on said base;

(b) a female member including a housing providing a pocket into which said extension is adapted to be telescopically received when said dental structure is mounted in said oral cavity and from which said extension is retracted when said dental structure is removed from said oral cavity, said female member adapted to be permanently mounted on said dental appliance;

(c) an element including a body of resilient, non-metallic material in the form of a lining complementary in outline to said pocket, said element having an open end, a closed end and a surface therebetween adapted to be mounted in said pocket of said female member whereby when said members are telescopically received said element will be disposed between and in surface-to-surface contact with both said extension and the wall of said pocket both to cushion said member and provide a tight fitting telescopic engagement and prevent any frictional contact of members when received and retracted;

(d) first mechanical attachment means carried by said element interacting with the surface of said extension; and (e) second mechanical attachment means carried by both said element and housing within said pocket, said second mechanical attachment means providing a mechanical securing capability greater than that provided by said first mechanical attachment means whereby when removing said dental appliance from its position of removable securement within said oral cavity said element will remain secured to said housing.

28. The dental structure of claim 27 wherein said second attachment means includes at least one projection in the form of a ridge formed on the outer surface of said lining and a cooperating number of depressions formed in said pocket.

29. The dental structure of claim 27 wherein said first attachment means includes a ridge formed on the inner surface of said lining near said open end, said ridge when said lining is received over said extension cooperating with a portion of said extension beyond the portion of maximum dimension when said members are telescopically received.

* * * * *